(12) United States Patent
Hill et al.

(10) Patent No.: US 7,507,535 B2
(45) Date of Patent: Mar. 24, 2009

(54) STRONG PCR PRIMERS AND PRIMER COCKTAILS

(75) Inventors: Janet Elizabeth Hill, Saskatchewan (CA); Sean Mathias Hemmingsen, Saskatchewan (CA); Jennifer Rae Town, Saskatchewan (CA)

(73) Assignee: National Research Council of Canada, Ottawa (CA)

( * ) Notice: Subject to any disclaimer, the term of this patent is extended or adjusted under 35 U.S.C. 154(b) by 248 days.

(21) Appl. No.: 11/448,078

(22) Filed: Jun. 7, 2006

(65) Prior Publication Data
US 2007/0072206 A1 Mar. 29, 2007

Related U.S. Application Data

(60) Provisional application No. 60/687,879, filed on Jun. 7, 2006.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/22.1; 536/24.3

(58) Field of Classification Search .............. 435/6, 435/91.2; 536/22.1, 24.3
See application file for complete search history.

(56) References Cited

U.S. PATENT DOCUMENTS 5,989,821 A * 11/1999 Goh et al. .................. 435/6

2004/0101860 A1 * 5/2004 Jones et al. ................ 435/6

* cited by examiner

Primary Examiner—Kenneth R. Horlick
Assistant Examiner—Joyce Tung
(74) Attorney, Agent, or Firm—Michael R. Williams; Ade & Company Inc.

(57) ABSTRACT

The invention disclosed relates to a PCR primer pair for amplication of chaperonin-60 (cpn60) targets having high G+C content and to a PCR primer "cocktail" to improve the representation of diverse sequences in chaperonin-60 based PCR product libraries derived from complex templates. In previous cpn60-based and 16S rDNA-based studies of mammalian intestinal microbiota, it has been observed that some classes of organisms such as the Actinobacteria, which are known through culture-based studies to be present in large numbers in these environments, are underrepresented or even absent from PCR product libraries. Using library sequence data and reference cpn60 sequence data from cpnDB, the chaperonin sequence database, we designed a pair of PCR primers which can be used alone for higher G+C content targets and, when used in combination with a previously developed degenerate, universal cpn60 primer pair, improve the representation of complex templates with high G+C content. We have validated these primers using a combination of traditional and quantitative real-time PCR on both artificially constructed complex templates and biological samples. The development and optimization of this primer cocktail represents a significant advance in our ability to generate cpn60 PCR product libraries which more closely represent the biodiversity in complex microbial communities.

6 Claims, 6 Drawing Sheets

STRONG PCR PRIMERS AND PRIMER COCKTAILS

PRIOR APPLICATION INFORMATION

This application claims the benefit of U.S. Provisional Application 60/687,879, filed Jun. 7, 2006.

BACKGROUND OF THE INVENTION

Complex microbial communities are often characterized by culture-independent methods, frequently based on 16S rRNA gene heterogeneity. Other gene targets can be exploited in these studies and the gene encoding the 60 kDa chaperonin, cpn60 (also called groEL or hsp60) has proven particularly useful since a phylogenetically informative fragment of the gene can be amplified with degenerate PCR primers and this target region (corresponding to nucleotides 274 and 828 of the *E. coli* cpn60 sequence) generally provides more discriminating power than 16S rRNA sequences, especially for closely related organisms (Goh et al., 1997; Goh et al., 2000; Brousseau et al., 2001). The cpn60 target has been employed in studies of complex microbial communities (Hill et al., 2002; Hill et al., 2005a; Hill et al., 2005b) and a large reference database of chaperonin sequences is now available (Hill et al., 2004).

Staley and Konopka (1985) used the term "great plate count anomaly" to describe the fact that many members of complex microbial communitites cannot be cultured in the laboratory and are therefore not represented in culture-based studies of these communitites. However, it has also been observed that some organisms that can be cultured from complex communities are not detected in culture-independent studies. For example, *Bifidobacterium* spp. have been identified in porcine and human feces at levels of 10 cfu/g (Benno et al., 1985; Hartemink and Rombouts, 1999). However, these organisms and other high G+C content organisms expected to be present, such as other Actinobacteria, were not detected in PCR and sequence-based studies of human or porcine feces using either the 16S rRNA gene or cpn60 as a target (Wilson and Blitchington, 1996; Suau et al., 1999; Hill et al., 2002). Furthermore, in the cpn60-based study, sequences identical to *Bifidobacterium* spp. were detected in the template DNA mixture using genus-specific primers, indicating that the failure to detect these sequences in the library was not completely accounted for by a failure to isolate genomic DNA from the organisms during template preparation from the starting material. Organisms in the *Bifidobacterium* genus have G+C contents approximately 60% (58-61% for 16S rRNA sequences of 24 strains; 59-64% for partial cpn60 sequences of 84 strains. A major contributor to the under-representation of high G+C organisms in PCR product libraries may in fact be the relative inefficiency of Taq DNA polymerase amplification from these templates.

Another likely contributing factor to the under-representation of high G+C content organisms in PCR product libraries is primer annealing bias. The primers used for amplification of bacterial 16S rRNA gene segments are generally non-degenerate because of the nearly perfect conservation of the annealing sites among bacteria and therefore one would not expect annealing bias to be a factor in these studies. However, the PCR primers used to amplify the 549-567 bp "universal target" region of the gene (H279 and H280)(Table 1) are degenerate and contain inosine residues in some positions to minimize degeneracy (Goh et al., 1996). There is an approximately 100-fold difference in the thermodynamic stability of inosine with each of the four nucleotides with I:C>I:A>I: G>I:T (Martin et al., 1985; Kawase et al., 1986). Stacking interactions between sequential inosine residues and variations in local structure of the DNA duplex can also affect the efficiency of base-pairing and introduce annealing bias when inosine-containing primers are used in PCR. We routinely use cpn60 amplification and sequencing in our laboratory for the identification of bacterial isolates and have observed that high G+C templates are more problematic and recalcitrant to amplification with the H279 and H280 primer pair. In fact, an analysis of approximately 1500 cpn60 universal target sequences generated in our laboratory (G+C content from 29% to 71%), led to the observation that the problematic templates were those with at least 58% G+C content.

We attempted to alleviate this problem by using the known fully degenerate versions of primers H279 and H280, containing N (A, C, T or G) in all of the positions currently occupied by inosine residues. Primers similar to this have been successfully applied to the amplification of *Bifidobacterium* cpn60 sequences (Jian et al., 2001), however we found that when applied to most templates, especially complex templates containing a mixture of genomes, these primers yielded unacceptable levels of inappropriate PCR products.

SUMMARY OF THE INVENTION

According to a first aspect of the invention, there is provided a primer pair for amplification of cpn60 targets having high G+C content comprising:

a first primer comprising a nucleotide sequence as set forth in SEQ ID NO. 1; and a second primer comprising a nucleotide sequence as set forth in SEQ ID NO. 2.

According to another aspect of the invention we have provided a cocktail of PCR primers containing the known primer pair H279 and H280 along with a novel PCR primer pair (H1612 and H1613) which would more efficiently amplify high G+C templates, to generate PCR product libraries from complex templates that more accurately represented the diversity of those samples.

DETAILED DESCRIPTION OF THE INVENTION

Figure 1A:
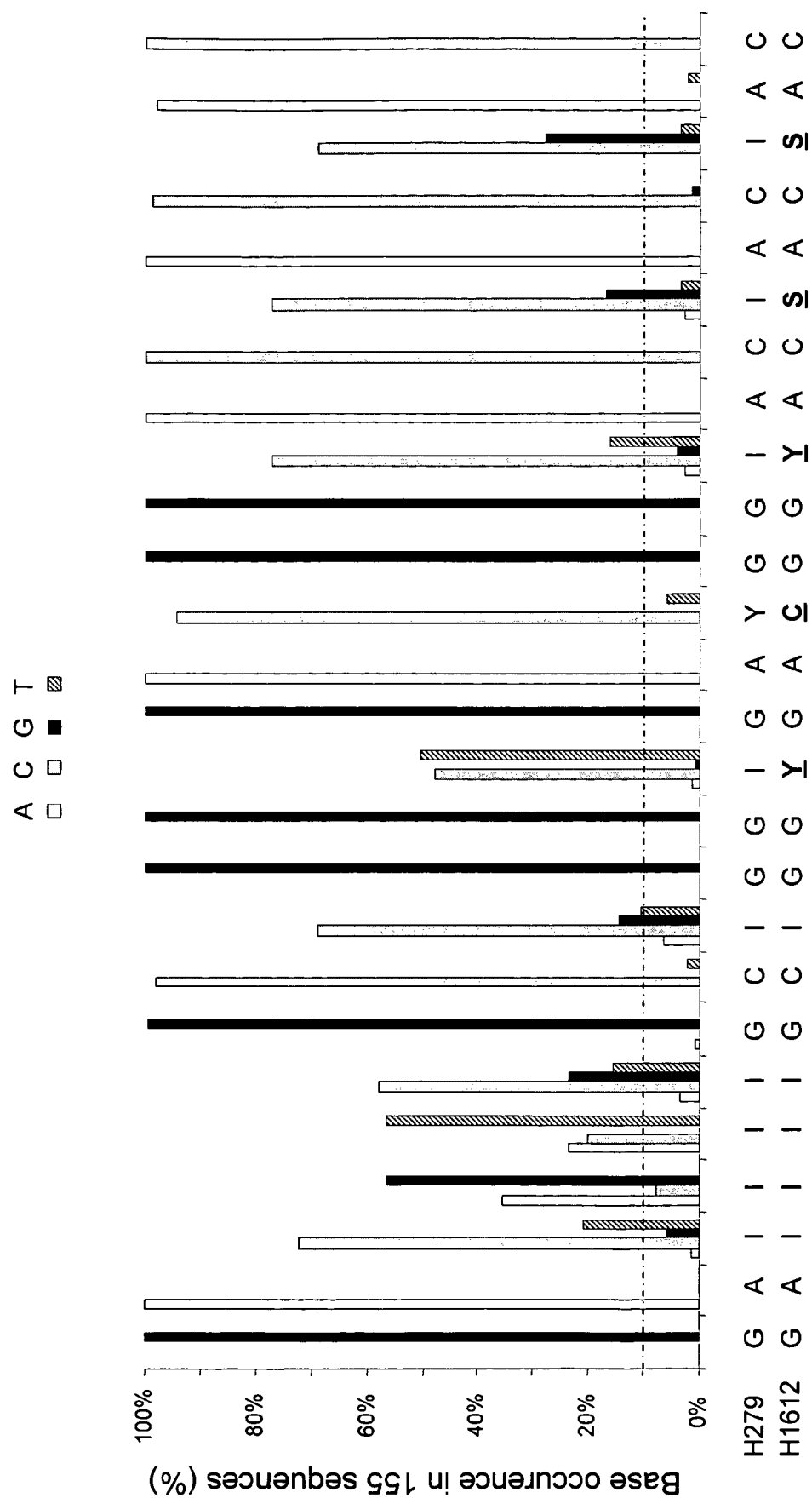
FIG. 1. Nucleotide frequencies in the H279/H280 primer annealing regions of cpn60 genes from organisms with G+C content of at least 58%. Full length cpn60 gene sequences from 155 organisms were aligned and the primer annealing sites for primers H279 and H280 were extracted. The frequency of occurrence of each nucleotide at each position of the primer annealing sites is shown. The sequences of H279 and H280, H1612 and H1613 are indicated (5' to 3') along the horizontal axes. Positions changed from H279/H280 in the design of H1612 and H1613 are underlined.

As used herein, "purified" does not require absolute purity but is instead intended as a relative definition. For example, purification of starting material or natural material to at least one order of magnitude, preferably two or three orders of magnitude is expressly contemplated as falling within the definition of "purified".

As used herein, the term "isolated" requires that the material be removed from its original environment.

Described herein is a primer pair for amplification of cpn60 targets having high G+C content comprising: a first primer comprising a nucleotide sequence as set forth in SEQ ID NO. 1; and a second primer comprising a nucleotide sequence as set forth in SEQ ID NO. 2. In other embodiments, the first primer may consist essentially of a nucleotide sequence as set forth in SEQ ID NO. 1; and the second primer may consist essentially of a nucleotide sequence as set forth in SEQ ID NO. 2. In yet other embodiments, the first primer may consist of a nucleotide sequence as set forth in SEQ ID NO. 1; and the second primer may consist of a nucleotide sequence as set forth in SEQ ID NO. 2.

In some embodiments, the target has a G+C content of at least 32%. In other embodiments, the target has a G+C content of about 32% to about 71%, from about 32% to about 68% or from about 32% to about 63%.

In another aspect of the invention, the above-described primers are used in a method of amplifying partial cpn60 sequences from genomic DNA comprising:
a) providing a sample comprising at least one bacterial target;
b) adding a primer pair for amplification of cpn60 targets having high G+C content comprising:
a first primer comprising a nucleotide sequence as set forth in SEQ ID NO. 1; and
a second primer comprising a nucleotide sequence as set forth in SEQ ID NO. 2; and
c) incubating the sample under conditions suitable for nucleotide amplification.

Examples of conditions suitable for nucleotide amplification are well-known to those of skill in the art and include enzymes, buffers, nucleotides, incubation times and temperatures and the like. Exemplary PCR conditions are shown for example in the description of FIG. 4 although other suitable conditions for nucleotide amplification will be readily apparent to one of skill in the art.

In some embodiments, a second primer pair comprising adding a third primer comprising a nucleotide sequence as set forth in SEQ ID NO. 3 and a fourth primer comprising a nucleotide sequence as set forth in SEQ ID NO. 4 is added to the mixture prior to step (c). The third primer may consist essentially of a nucleotide sequence as set forth in SEQ ID NO. 3 and the fourth primer may consist essentially of a nucleotide sequence as set forth in SEQ ID NO. 4. In other embodiments, the third primer may consist of a nucleotide sequence as set forth in SEQ ID NO. 3 and the fourth primer may consist of a nucleotide sequence as set forth in SEQ ID NO. 4.

As will be appreciated by one of skill in the art, as used herein, 'first primer', 'second primer', 'third primer' and 'fourth primer' are relative terms and serve to identify the primers but do not indicate a required order of addition.

As discussed below, the first primer and the second primer may be added to the sample at a concentration at a ratio of from 1:1 to 10:1 compared to the concentration of the third primer and the fourth primer in the sample. Specifically, the ratio may be from 1:1 to 10:1 or from 1:1 to 9:1 or from 1:1 to 8:1 or from 1:1 to 7:1 or from 1:1 to 6:1 or from 1:1 to 5:1 or from 1:1 to 4:1 or from 1:1 to 3:1 or from 1:1 to 2:1. This mixture comprising two primer pairs can be used for amplification of partial cpn60 sequences from organisms of both high and low G+C content as discussed below.

Examples of suitable bacterial targets include those bacteria having a conserved cpn60 sequence which can be amplified under suitable conditions using primer pairs H279/H280 and/or H1612/H1613. Suitable bacterial targets will be well known to one of skill in the art and exemplary examples of such are provided herein for example in Table 1.

Examples of suitable samples include but are by no means limited to soil, sludge, waste water, bodily fluids, intestinal contents and the like. As discussed below, the primer pair described herein can be used alone or in combination with H279/H280 for many purposes, for example, for following population dynamics of a complex bacterial community, determining effectiveness of antimicrobials, determining the effect of feeding regimes on gut flora and the like.

Typically, a primer pair includes a primer which is complementary to the negative (−) strand of the polymorphic locus, and the other is complementary to the positive (+) strand.

Figure 1B:
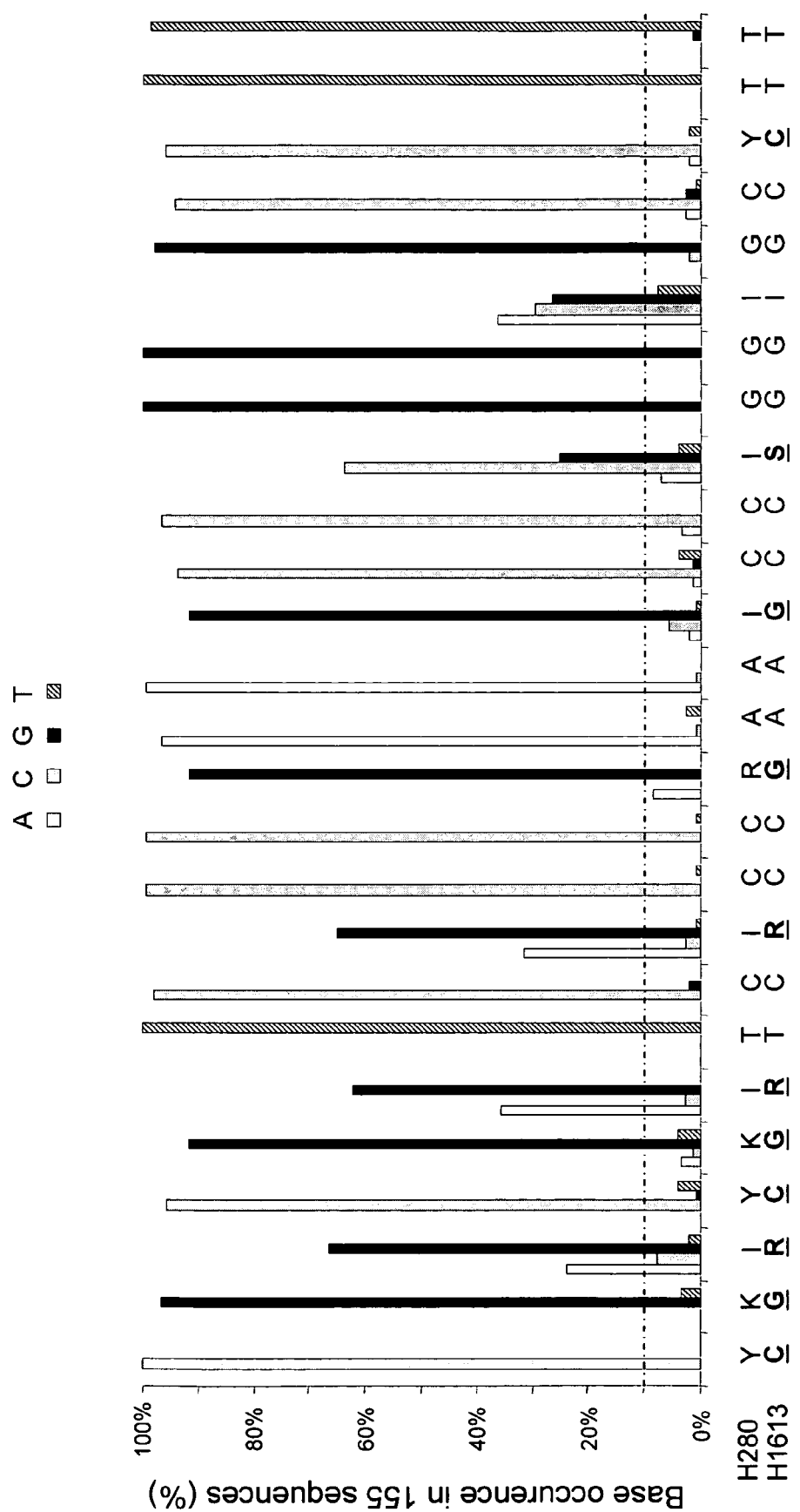

The availability of a large reference data set of cpn60 sequences (Hill et al., 2004) made it possible to study the primer annealing sites in organisms with high G+C content. A phylogenetic group of organisms can have a characteristic G+C content; however, G+C content can also vary within a phylogenetic group. Phylogenetically distant organisms can have identical G+C contents. We aligned 155 full-length cpn60 sequences (54 genera) with G+C contents of at least 58%, identified the primer annealing sites for H279 and H280 and calculated the frequency of occurrence of A, T, G and C at each position (FIG. 1). By comparing the high G+C template primer annealing sites with H279 and H280 and considering frequencies of at least 10% to be significant, we designed the novel PCR primer pair H1612 and H1613. The net result was the reduction from 9 to 5 inosine residues in the forward primer and 6 to 1 inosine in the reverse primer. The degeneracy of the forward primer increased from 2 to 16 and the reverse primer decrease in degeneracy from 64 to 16 (Table 1). Inosine can base pair with each of the 4 naturally occurring bases. In the original primers, inosine residues were introduced at positions in the sequence where all 4 bases occurred. Alternatively, introducing all 4 naturally occurring bases at these sites would have produced a degeneracy of 4 at each site since the primer pool synthesized would include 4 distinct sequences at a given site. If 2 sites were completely degenerate, the total degeneracy would be 16 fold; if 3 sites, the total would be 64 fold etc. Going in the reverse direction, if we changed an inosine residue to an A or a G, we would increase the degeneracy of the primer by 2 fold.

Figure 2:
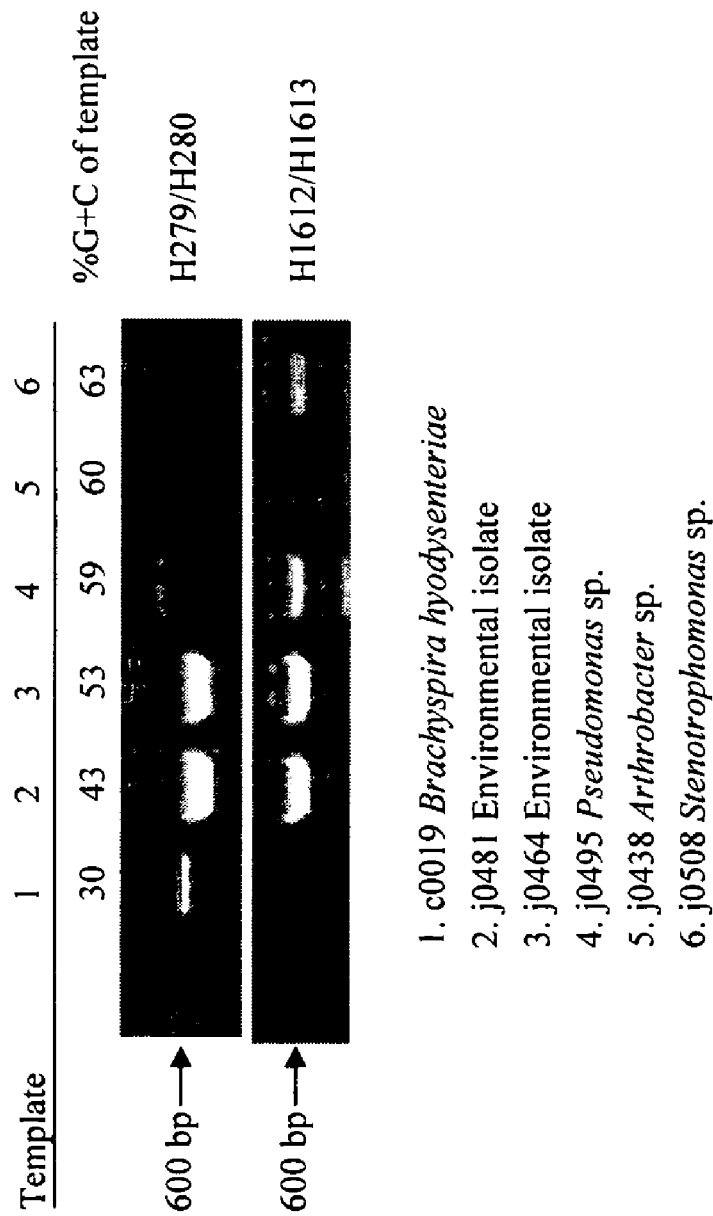
FIG. 2. Five nanograms of purified genomic DNA from each of the bacterial isolates was used as template in a 40 cycle PCR reaction using an annealing temperature of 46° C.

In the process of validating the primers for PCR use, we applied them to individual bacterial templates ranging in G+C content from 30% to 63%. As illustrated in FIG. 2, primers H279/H280 amplified cpn60 sequences from the first 3 templates but failed to amplify from templates with G+C content of >53%. Primers H1612/H1613 amplified all templates with the exception of *Brachyspira hyodysenteriae* (G+C content of 30%). Primers H1612/H1613 fail to amplify some low G+C templates and they may fail to amplify many or all templates with similarly low G+C contents.

Figure 3:
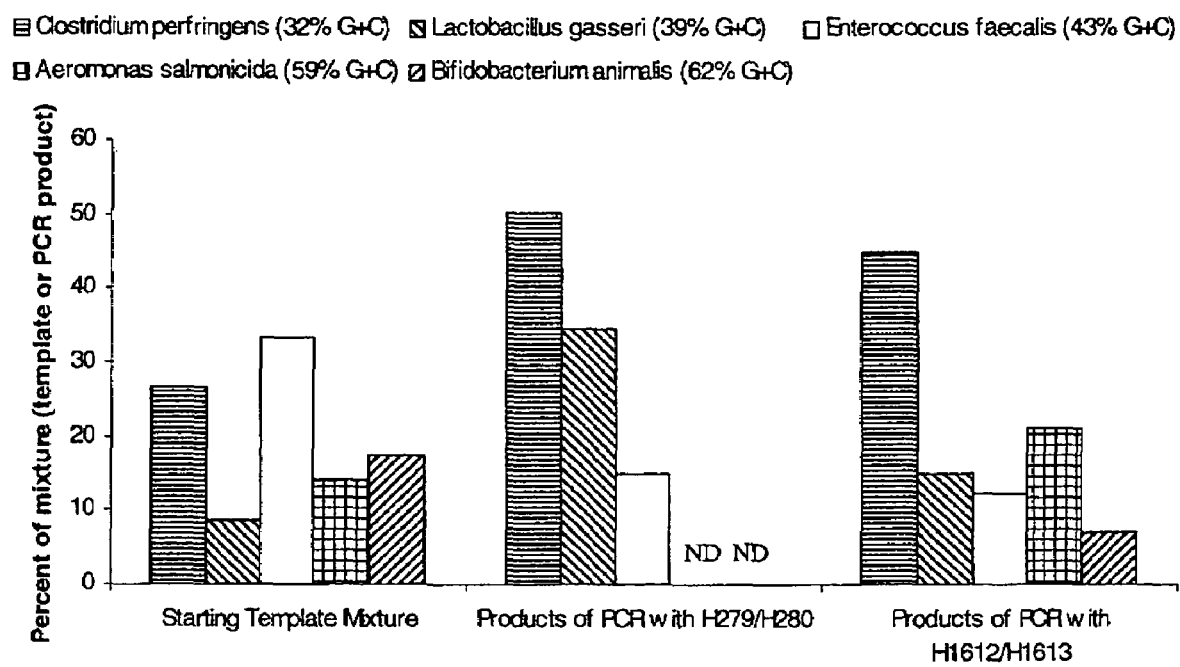
FIG. 3. Results of amplification of a mixture of 5 bacterial genomic DNA templates with primers H279/H280 or primers H1612/H1613. The higher G+C content templates (*A. salmonicida* and *B. animalis*) are only detected after amplification with H1612/H1613. The figure shows the average of 4 experiments (ND=not detected).

We also applied primers H11612/H1613 to mixtures of DNA templates with a range of G+C contents to determine if all of the component templates would be amplified and thus be detectable in the PCR product mixture produced. A mixture of 5 bacterial genomic DNA samples was created according to the following proportions: 27% *Clostridium perfringens*, 9% *Lactobacillus gasseri*, 33% *Enterococcus faecalis*, 14% *Aeromonas salmonicida* and 17% *Bifidobacterium animalis*. PCR reactions were performed using either primers H279/H280 or H1612/H1613. The amount of PCR product corresponding to each template in the reaction products after 40 cycles of PCR was determined using quantitative real-time PCR. As illustrated in FIG. 3, after amplification with the H279/H280, PCR products from the *A. salmonicida* and *B. animalis* templates (59% and 62% G+C respectively) were not detected, indicating that these templates were not amplified with H279/H280. However, after amplification with the

TABLE 1

PCR primers for universal and species-specific amplifications

| Primer | Target | Sequence | Degeneracy | $T_{anneal}$ (° C.) |
|---|---|---|---|---|
| H279 |  | GAIIIIGCIGGIGAYGGIACIACIAC | 2 |  |
| H280 |  | YKIYKITCICCRAAICCIGGIGCYTT | 64 |  |
| H1612 |  | GAIIIIGCIGGYGACGGYACSACSAC | 16 |  |
| H1613 |  | CGRCGRTCRCCGAAGCCSGGIGCCTT | 16 |  |
| CPF41U19 | C. perfringens | AAATGTAACAGCAGGGGCA | 1 | 59 |
| CPF160L21 |  | TGAAATTGCAGCAACTCTAGC | 1 |  |
| EFC227U21 | E. faecalis | AAGTTGGTAACGACGGCGTAA | 1 | 62 |
| EFC306L21 |  | GATAAATAACCGCGGTCGAAT | 1 |  |
| LGS134U21 | L. gasseri | ACAAGGTAAGCACTAAGGATG | 1 | 55 |
| LGS269L21 |  | CCCTTTGATTCCTCAATTGTG | 1 |  |
| H1592 | A. salmonicida | YACCATCTCYGCMAACTC | 8 | 59 |
| H1593 |  | TTCTTRTCVACCAGCAGGAT | 6 |  |
| BAN104U21 | B. animalis | CTCTCGTCAAGCAGCTTGTCG | 1 | 62 |
| BAN343L21 |  | GGCCGTCTGGTCTTCCGCATT | 1 |  |

The following data summarizes experimental evidence demonstrating that the oligonucleotide primers H11612 (SEQ ID NO. 1) and H11613 (SEQ ID NO. 2) ("Strong Primers") can be used by themselves to amplify partial cpn60 sequences from DNA templates ranging in G+C content from (at least) 32% to 63%.

Oligonucleotides H11612 and H11613 were designed based on the analysis of cpn60 sequences from source organisms with G+C content of at least 58%. The primers anneal to templates in the same regions as H279 (SEQ ID NO. 3)/H280 (SEQ ID NO. 4) and amplify a region of the cpn60 gene corresponding to nucleotides 274-828 of the *Escherichia coli* cpn60 gene.

H1612/H1613 primer combination, all templates could be detected in the PCR product pool.

The results presented in FIGS. 2 and 3 demonstrate that the H1612/H1613 primer pair can be used to amplify partial cpn60 sequences from genomic DNA templates ranging in G+C content from 32% to 63%. We anticipate, based on sequence analysis and experiments to date, that they will work on even higher G+C contents. Specifically, we have used these primers to amplify cpn60 sequences with a 68% G+C content from an environmental organism present in muck soil that was amended with fish emulsion.

In order to test the efficacy of novel primer pair H1612/H1613 in combination with the H279/H280 primer pair, we created a mixture of genomic DNA from 5 species, ranging in cpn60 G+C content from 32% to 62% (Table 2).

TABLE 2

Genomic DNA used to make template mixtures.

| Organism | cpn60 G+C content | Genbank Accession |
|---|---|---|
| *Clostridium perfringens* (poultry isolate) | 32% | AY835618 |
| *Lactobacillus gasseri* ATCC 9857 | 39% | AY123652 |
| *Enterococcus faecalis* ATCC 49332 | 43% | DQ074968 |
| *Aeromonas salmonicida* A449 | 59% | DQ074967 |
| *Bifidobacterium animalis* ATCC 27536 | 62% | AY488181 |

Three independent mixtures of the 5 species were made for 4 replicates of the amplification experiment. The composition of each mixture was determined by quantitative PCR using the species-specific primers described in Table 1, using a standard curve generated from a dilution series of cloned cpn60 PCR products for each species (Dumonceaux et al 2005) and the proportion of the total population comprised by each of the species was calculated (Table 3).

TABLE 3

Compositions of genomic DNA template mixtures
Number of genomes (fraction of total)

| Expt # | C. perfringens | L. gasseri | E. faecalis | A. salmonicida | B. animalis | total genomes |
|---|---|---|---|---|---|---|
| 1 | $3.48 \times 10^4$ (0.30) | $5.13 \times 10^3$ (0.04) | $4.22 \times 10^4$ (0.36) | $2.05 \times 10^4$ (0.18) | $1.33 \times 10^4$ (0.11) | $1.16 \times 10^5$ |
| 2 | $3.77 \times 10^4$ (0.28) | $9.23 \times 10^3$ (0.07) | $4.69 \times 10^4$ (0.35) | $2.73 \times 10^4$ (0.21) | $1.14 \times 10^4$ (0.21) | $1.33 \times 10^5$ |
| 3* | $8.61 \times 10^4$ (0.26) | $3.26 \times 10^4$ (0.10) | $1.09 \times 10^5$ (0.32) | $4.08 \times 10^4$ (0.12) | $6.72 \times 10^4$ (0.20) | $3.36 \times 10^5$ |
| 4* | $8.61 \times 10^4$ (0.26) | $3.26 \times 10^4$ (0.10) | $1.09 \times 10^5$ (0.32) | $4.08 \times 10^4$ (0.12) | $6.72 \times 10^4$ (0.20) | $3.36 \times 10^5$ |

*identical template mixture used for technical replicate of PCR

Sample mixtures were amplified with various ratios of PCR primers H279/H280:H1612/H1613 (10:0, 7:1, 3:1, 1:1, 1:3, 1:7, and 0:10 molar ratios) at each of 4 annealing temperatures (42° C., 46.5° C., 50.4° C., 56° C.) and the products were pooled. To create complex microbial community libraries, we routinely do the PCR amplifications over a range of temperatures since we have previously demonstrated that annealing temperature affects library composition (Hill et al., 2002) and our goal is to maximize diversity in the library. PCR products derived from each of the 5 templates were quantified using the species-specific PCR primers shown in Table 1 and expressed as proportions of the total PCR product mixture.

Figure 4:
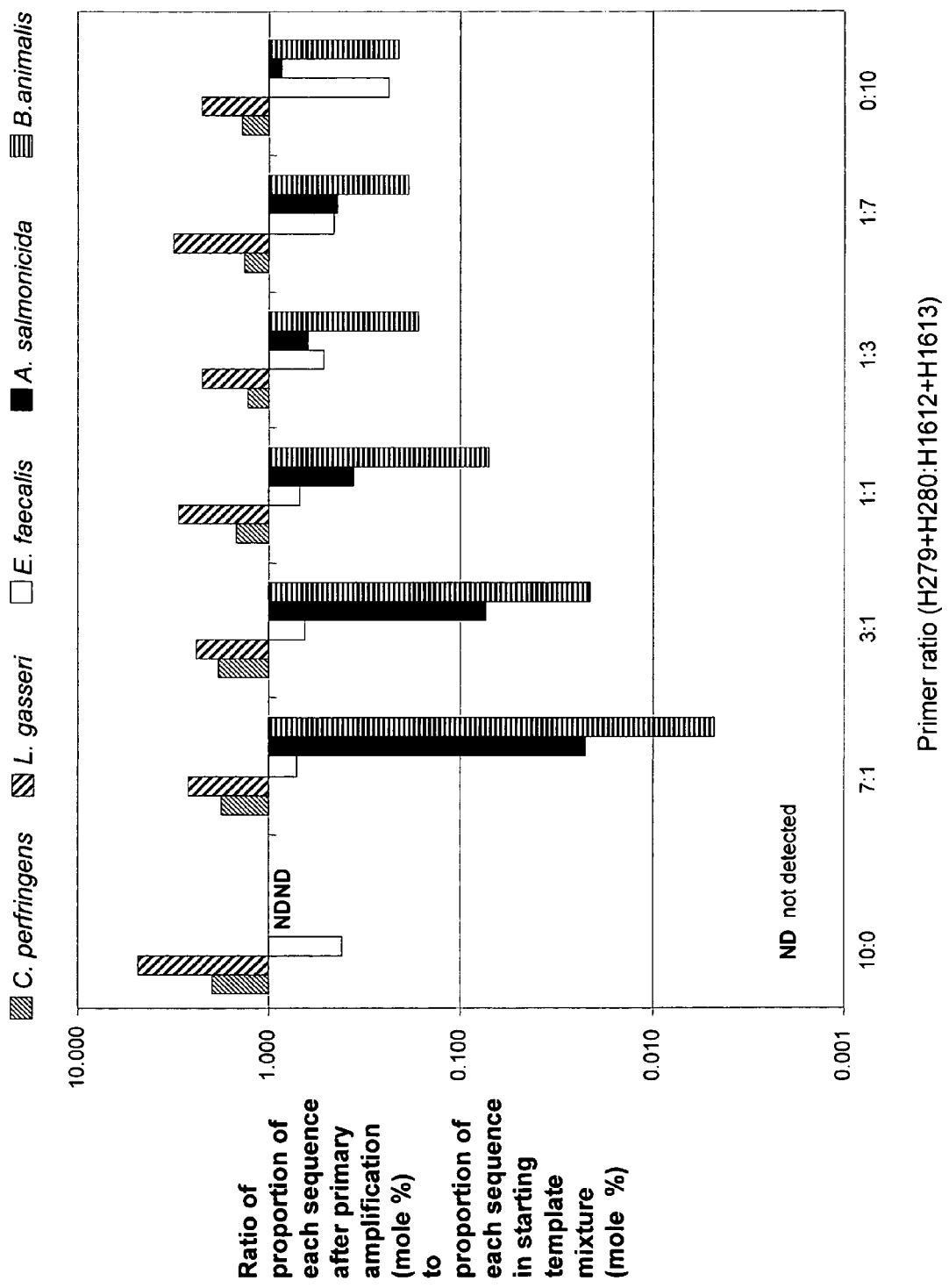
FIG. 4. Effects of primer composition on amplification bias in a manufactured mixture of genomic DNA from 5 species. Mixtures of genomic DNA from 5 species (Table 1) were created according to Table 2. Primary PCR reactions (containing 800 nM total primer concentration, 2.5 u Taq DNA polymerase, 2.5 mM MgCl2, 50 mM KCl, 10 mM Tris-HCl pH 8.3, 250 μM of each of the dNTPs) were conducted at each of 4 annealing temperatures (42, 46.5, 50.4, 56) using thermocycling parameters of (95° C. for 2 min followed by 40 cycles of (95° C. for 30 sec, 30 sec at Tanneal, 72° C. for 30 sec) and final extension of 2 min at 72° C.). Primary PCR products were pooled and agarose gel purified prior to quantitative real-time PCR. An aliquot of a $10^{-5}$ dilution of the primary PCR product (necessary to bring the target copy number within range of the standard curve) was used as template in the quantitative PCR reactions. Quantitative PCR reactions (containing 500 nM each primer and 1×Platinum SYBR green qPCR SuperMix UDG (Invitrogen)) were conducted on a BioRad iCycler according to the following protocol: 50° C. for 2 min, 3 min at 95° C., 40 cycles of (30 sec at 95° C., 30 sec at Tanneal (see Table 1), 30 sec at 72° C.). A melt curve was conducted following quantitative PCR to confirm PCR product identity and purity. Copy numbers of each target were quantitated according to a standard curve of diluted plasmid containing cloned cpn60 sequences from the target. The proportion (mol %) of the mixture corresponding to each species was calculated before and after PCR amplification with various ratios of H279/H280:H1612/H1613. The ratio of these proportions was calculated in each of 4 experiments and the average of the 4 experiments is presented. ND=not detected.

FIG. 4 shows the relative representations of each of the 5 templates pre- and post-amplification. The *Aeromonas salmonicida* and *Bifidobacterium animalis* templates which had each accounted for 10-20% of the original template mixtures were undetectable by quantitative PCR in experiments where the H279/H280 primer pair was used exclusively. As the relative amount of H1612/H1613 primer increased to a 1:3 ratio, the representation of these G+C-rich templates improved. Further skewing of the primer cocktail ratio beyond 1:3 (to 1:7 and 0:10) did not improve the representation of these templates. After amplification with a 1:3 ratio of H279/H280: H1612/H1613, the proportions of each template in the amplified PCR product population were within a log of their proportions in the original template.

Figure 5:
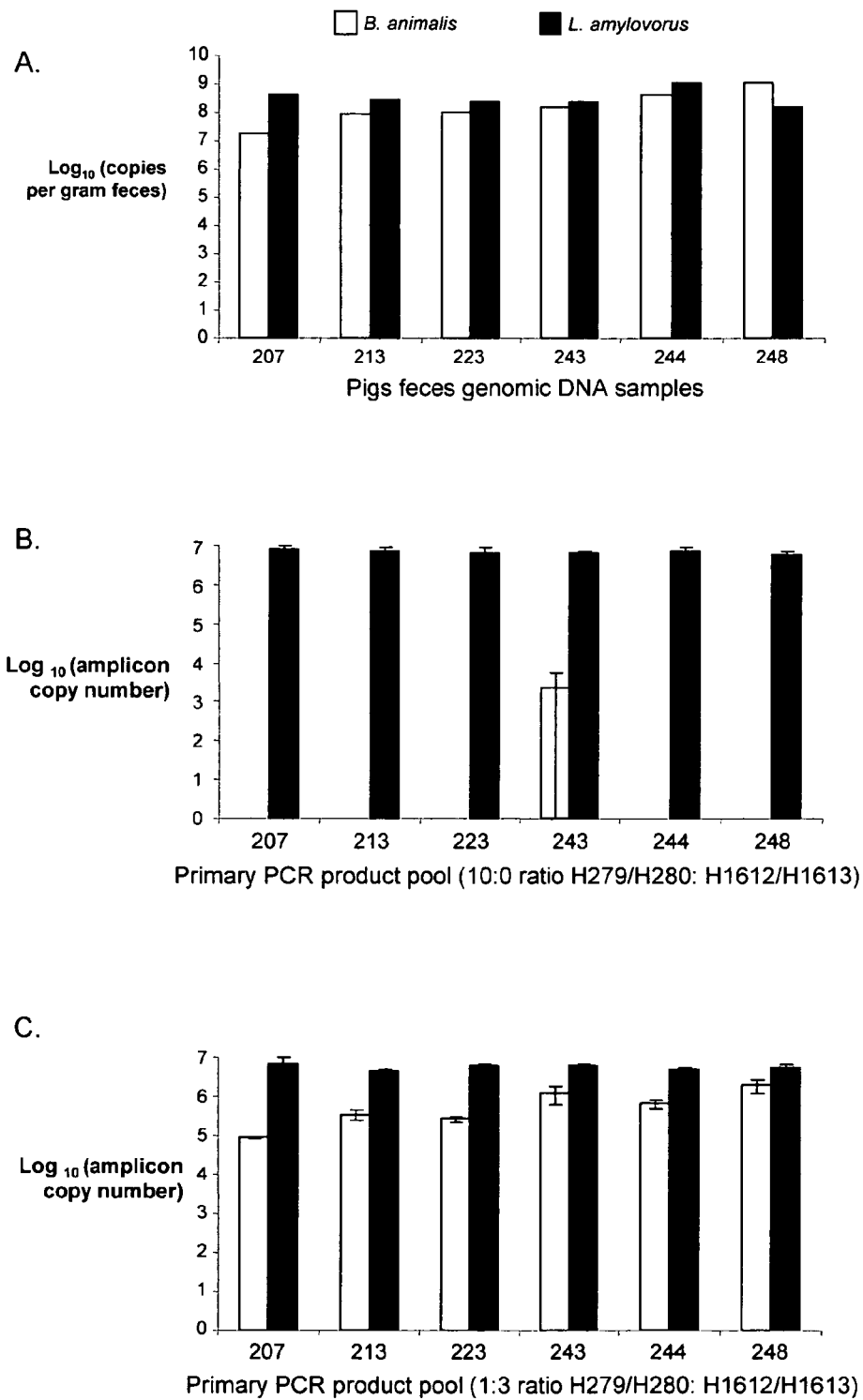
FIG. 5. Effects of primer composition on amplification bias in pig feces. Genomic DNA was extracted from 400 mg of feces from each of 6 pigs (fed basal control diet based on wheat, barley and soybean meal). Species specific PCR primers were used to quantitate *B. animalis* and *L. amylovorus* targets in the genomic DNA samples (PCR conditions and parameters are described in FIG. 4) and expressed as target copy number per gram of feces (A). cpn60 amplification from these templates was conducted using either a 10:0 (B) or 1:3 (C) mixture of H279/H280:H1612/H1613 according to the protocol in FIG. 4. Primary PCR reactions were pooled, agarose gel-purified and diluted ($10^{-5}$) prior to quantitative PCR (necessary to bring the target copy number within range of the standard curve). Error bars in (B) and (C) indicate the standard deviation observed between two experiments. For sample 243, *B. animalis* was detected in the 10:0 amplification product in only one of two experiments.

To demonstrate the effectiveness of the primer cocktail (1:3 ratio of H279/H280:H1612/H1613) for amplification of sequences from a natural microbial community, we obtained total genomic DNA from fecal samples from 6 pigs. Using species-specific PCR primers we quantitated the amount of *L. amylovorus* and *B. animalis* in the samples (FIG. 5A). In agreement with culture-based studies of pig fecal microbial populations, we found that these targets were present at approximately 10 to 10 genomes per gram. After PCR amplification with a 10:0 ratio of H279/H280: H1612/H1613 primers (FIG. 5B), we conducted quantitative real-time PCR with species-specific PCR primers to determine the relative amounts of *L. amylovorus* and *B. animalis* targets in the PCR product pool. While the *L. amylovorus* target was easily detectable in the primary PCR product pool, we only detected *B. animalis* amplicons in one of two independent amplifications from pig 243 and the small amount detected was at the extreme lower limit of the standard curve (~$10^3$ copies). In contrast, an examination of the PCR product pool produced using the 1:3 ratio of H279/H280: H1612/H1613 primers showed that *B. animalis* PCR products were present in relative quantities to the *L. amylovorus* target similar to that observed in the starting material (FIG. 5C). A library created from the PCR product pool created with the 1:3 cocktail of H279/H280: H612/H11613 (FIG. 5 C) would be much more likely to contain *B. animalis* sequences than a library created from the PCR product pool created with the H279/H280 primers alone (FIG. 5B). In fact, a cpn60 library recently created from pig intestinal contents using the primer cocktail presented here does in fact contain *Bifidobacterium* sequences.

An essential first step in the study of a microbial community is an inventory of its constituents. This inventory can subsequently be used in the design of molecular tools for the quantification and monitoring of population members. Our observations indicate that application of the 1:3H279/H280: H1612/H1613 primer cocktail will allow the construction of cpn60 PCR product libraries that more accurately represent the diversity of a microbial population than was possible with the H279/H280 primers alone. These libraries will provide an excellent starting point for more intensive studies of microbial population dynamics.

Environments that we have examined include the microbiota of soils that suppress plant pathogens, the microbiota of the human vagina, the microbiota of activated sludge waste water in pulp and paper mills, the microbiota in intestinal tracts of animals fed control diets or diets that included antimicrobials. Other suitable environments will be apparent to those of skill in the art.

While the preferred embodiments of the invention have been described above, it will be recognized and understood that various modifications may be made therein, and the appended claims are intended to cover all such modifications which may fall within the spirit and scope of the invention.

REFERENCES

Benno, Y., Endo, K., Suzuki, K., Mitsuoka, T., and Namioka, S. (1985) Use of nonprotein nitrogen in pigs: effects of dietary urea on the intestinal microflora. *Am J Vet Res* 46: 959-962.

Brousseau, R., Hill, J. E., Prefontaine, G., Goh, S. H., Harel, J., and Hemmingsen, S. M. (2001) *Streptococcus suis* serotypes characterized by analysis of chaperonin 60 gene sequences. *Appl Environ Microbiol* 67: 4828-4833.

Dumonceaux, T. J., Hill, J. E., Briggs, S. A., Amoako, K. K., Hemmingsen, S. M. and Van Kessel, A. G. (2005) Enumeration of specific bacterial populations in complex intestinal communities using quantitative PCR based on the chaperonin-60 target. *J Microbiol Meth*, In Press.

Goh, S. H., Facklam, R. R., Chang, M., Hill, J. E., Tyrrell, G. J., Burns, E. C. et al. (2000) Identification of *enterococcus* species and phenotypically similar *lactococcus* and *vagococcus* species by reverse checkerboard hybridization to chaperonin 60 gene sequences. *J Clin Microbiol* 38: 3953-3959.

Goh, S. H., Potter, S., Wood, J. O., Hemmingsen, S. M., Reynolds, R. P., and Chow, A. W. (1996) HSP60 gene sequences as universal targets for microbial species identification: Studies with coagulase-negative staphylococci. *Journal of Clinical Microbiology* 34: 818-823.

Goh, S. H., Santucci, Z., Kloos, W. E., Faltyn, M., George, C. G., Driedger, D., and Hemmingsen, S. M. (1997) Identification of *Staphylococcus* species and subspecies *using* the Chaperonin-60 gene identification method and reverse checkerboard hybridization. *J Clin Microbiol* 35: 31163121.

Hartemink, R. and Rombouts, F. M. (1999) Comparison of media for the detection of bifidobacteria, lactobacilli and total anaerobes from faecal samples. *J Microbiol Methods* 36:181-192.

Hill J E, Goh S H, Money D M, Doyle M, Li A, Crosby W L, Links M, Leung A, Chan D and Hemmingsen S M. (2005a). Characterization of vaginal microflora of healthy, non-pregnant women using chaperonin-60 sequence-based methods. *Am. J. Obstet. Gynecol.* In Press.

Hill J E, Hemmingsen S M, Goldade B, Dumonceaux, T, Klassen, J, Zijlstra R T, Goh S H and Van Kessel A G. (2005b). Comparison of ileum microflora of pigs fed corn, wheat or barley-based diets using chaperonin-60 sequencing and quantitative PCR. *Appl. Environ. Microbiol.* 71(2): 867-75.

Hill, J. E., Penny, S. L., Crowell, K. G., Goh, S. H., and Hemmingsen, S. M. (2004) cpnDB: a chaperonin sequence database. Genome Res 14: 1669-1675.

Hill, J. E., Seipp, R. P., Betts, M., Hawkins, L., Van Kessel, A. G., Crosby, W. L., and Hemmingsen, S. M. (2002) Extensive profiling of a complex microbial community by high-throughput sequencing. *Appl Environ Microbiol* 68: 3055-3066.

Jian, W., Zhu, L., and Dong, X. (2001) New approach to phylogenetic analysis of the genus *Bifidobacterium* based on partial HSP60 gene sequences. *Int J Syst Evol Microbiol* 51: 16331638.

Kawase, Y., Iwai, S., Inoue, H., Miura, K., and Ohtsuka, E. (1986) Studies on nucleic acid interactions. I. Stabilities of mini-duplexes (dG2A4XA4G2-dC2T4YT4C2) and self-complementary d(GGGAAXYTTCCC) containing deoxyinosine and other mismatched bases. *Nucleic Acids Res* 14: 7727-7736.

Martin, F. H., Castro, M. M., boul-ela, F., and Tinoco, I., Jr. (1985) Base pairing involving deoxyinosine: implications for probe design. *Nucleic Acids Res* 13: 8927-8938.

Staley, J. T. and Konopka, A. (1985) Measurement of in situ activities of nonphotosynthetic microorganisms in aquatic and terrestrial habitats. *Annu Rev Microbiol* 39: 321-346.

Suau, A., Bonnet, R., Sutren, M., Godon, J. J., Gibson, G. R., Collins, M. D., and Dore, J. (1999) Direct analysis of genes encoding 16S rRNA from complex communities reveals many novel molecular species within the human gut. *Appl Environ Microbiol* 65: 4799-4807.

Wilson, K. H. and Blitchington, R. B. (1996) Human colonic biota studied by ribosomal DNA sequence analysis. *Appl Environ Microbiol* 62: 2273-2278.

---

The invention claimed is:

1. A primer pair for amplification of cpn60 targets having high G+C content comprising:
   a first primer comprising the nucleotide sequence as set forth in SEQ ID NO. 1; and
   a second primer comprising the nucleotide sequence as set forth in SEQ ID NO. 2.

2. A method of amplifying partial cpn60 sequences from genomic DNA comprising:
   a) providing a sample comprising at least one bacterial cpn60 DNA target;
   b) adding a primer pair for amplification of cpn60 DNA targets comprising:
      a first primer comprising the nucleotide sequence as set forth in SEQ ID NO. 1; and
      a second primer comprising the nucleotide sequence as set forth in SEQ ID NO. 2; and
   c) incubating the sample under conditions suitable for DNA amplification.

3. The method according to claim 2 wherein the DNA target has a G+C content of 32% to 71%.

4. The method according to claim 2 wherein the DNA target has a G+C content of at least 32%.

5. The method according to claim 2 further comprising adding a third primer comprising the nucleotide sequence as set forth in SEQ ID NO. 3 and a fourth primer comprising the nucleotide sequence as set forth in SEQ ID NO. 4 prior to step (c).

6. The method according to claim 5 wherein the first primer and the second primer are added to the sample at a concentration at a ratio of from 1:1 to 10:1 compared to the concentration of the third primer and the fourth primer in the sample.

* * * * *

SEQUENCE LISTING

```
<160> NUMBER OF SEQ ID NOS: 14

<210> SEQ ID NO 1
<211> LENGTH: 26
<212> TYPE: DNA
<213> ORGANISM: artificial
<220> FEATURE:
<223> OTHER INFORMATION: high G+C content consensus primer
<220> FEATURE:
<221> NAME/KEY: misc_feature
<222> LOCATION: (3)..(6)
<223> OTHER INFORMATION: inosine residues (see table 1)
<220> FEATURE:
<221> NAME/KEY: misc_feature
<222> LOCATION: (9)..(9)
<223> OTHER INFORMATION: inosine residues (see table 1)

<400> SEQUENCE: 1
gannnngcng gygacggyac sacsac                                          26

<210> SEQ ID NO 2
<211> LENGTH: 26
<212> TYPE: DNA
```

<213> ORGANISM: artificial
<220> FEATURE:
<223> OTHER INFORMATION: high G+C content consensus primer
<220> FEATURE:
<221> NAME/KEY: misc_feature
<222> LOCATION: (21)..(21)
<223> OTHER INFORMATION: Inosine residue (see table 1)

<400> SEQUENCE: 2
cgrcgrtcrc cgaagccsgg ngcctt                                      26

<210> SEQ ID NO 3
<211> LENGTH: 26
<212> TYPE: DNA
<213> ORGANISM: artificial
<220> FEATURE:
<223> OTHER INFORMATION: consensus sequence
<220> FEATURE:
<221> NAME/KEY: misc_feature
<222> LOCATION: (3)..(6)
<223> OTHER INFORMATION: Inosine residues (see table 1)
<220> FEATURE:
<221> NAME/KEY: misc_feature
<222> LOCATION: (9)..(9)
<223> OTHER INFORMATION: Inosine residue (see table 1)
<220> FEATURE:
<221> NAME/KEY: misc_feature
<222> LOCATION: (12)..(12)
<223> OTHER INFORMATION: Inosine residue (see table 1)
<220> FEATURE:
<221> NAME/KEY: misc_feature
<222> LOCATION: (18)..(18)
<223> OTHER INFORMATION: Inosine residue (see table 1)
<220> FEATURE:
<221> NAME/KEY: misc_feature
<222> LOCATION: (21)..(21)
<223> OTHER INFORMATION: Inosine residue (see table 1)
<220> FEATURE:
<221> NAME/KEY: misc_feature
<222> LOCATION: (24)..(24)
<223> OTHER INFORMATION: Inosine residue (see table 1)

<400> SEQUENCE: 3
gannnngcng gngayggnac nacnac                                      26

<210> SEQ ID NO 4
<211> LENGTH: 26
<212> TYPE: DNA
<213> ORGANISM: artificial
<220> FEATURE:
<223> OTHER INFORMATION: consensus sequence
<220> FEATURE:
<221> NAME/KEY: misc_feature
<222> LOCATION: (3)..(3)
<223> OTHER INFORMATION: Inosine
<220> FEATURE:
<221> NAME/KEY: misc_feature
<222> LOCATION: (6)..(6)
<223> OTHER INFORMATION: Inosine
<220> FEATURE:
<221> NAME/KEY: misc_feature
<222> LOCATION: (9)..(9)
<223> OTHER INFORMATION: Inosine
<220> FEATURE:
<221> NAME/KEY: misc_feature
<222> LOCATION: (15)..(15)
<223> OTHER INFORMATION: Inosine
<220> FEATURE:
<221> NAME/KEY: misc_feature
<222> LOCATION: (18)..(18)
<223> OTHER INFORMATION: Inosine
<220> FEATURE:
<221> NAME/KEY: misc_feature
<222> LOCATION: (21)..(21)
<223> OTHER INFORMATION: Inosine

```
<400> SEQUENCE: 4
yknykntcnc craanccngg ngcytt                              26

<210> SEQ ID NO 5
<211> LENGTH: 19
<212> TYPE: DNA
<213> ORGANISM: Clostridium perfringens

<400> SEQUENCE: 5
aaatgtaaca gcagggca                                        19

<210> SEQ ID NO 6
<211> LENGTH: 21
<212> TYPE: DNA
<213> ORGANISM: Clostridium perfringens

<400> SEQUENCE: 6
tgaaattgca gcaactctag c                                    21

<210> SEQ ID NO 7
<211> LENGTH: 21
<212> TYPE: DNA
<213> ORGANISM: Enterococcus faecalis

<400> SEQUENCE: 7
aagttggtaa cgacggcgta a                                    21

<210> SEQ ID NO 8
<211> LENGTH: 21
<212> TYPE: DNA
<213> ORGANISM: Enterococcus faecalis

<400> SEQUENCE: 8
gataaataac cgcggtcgaa t                                    21

<210> SEQ ID NO 9
<211> LENGTH: 21
<212> TYPE: DNA
<213> ORGANISM: Lactobacillus gasseri

<400> SEQUENCE: 9
acaaggtaag cactaaggat g                                    21

<210> SEQ ID NO 10
<211> LENGTH: 21
<212> TYPE: DNA
<213> ORGANISM: Lactobacillus gasseri

<400> SEQUENCE: 10
ccctttgatt cctcaattgt g                                    21

<210> SEQ ID NO 11
<211> LENGTH: 18
<212> TYPE: DNA
<213> ORGANISM: Aeromonas salmonicida

<400> SEQUENCE: 11
yaccatctcy gcmaactc                                        18

<210> SEQ ID NO 12
<211> LENGTH: 20
<212> TYPE: DNA
```

-continued

```
<213> ORGANISM: Aeromonas salmonicida

<400> SEQUENCE: 12
ttcttrtcva ccagcaggat                                               20

<210> SEQ ID NO 13
<211> LENGTH: 21
<212> TYPE: DNA
<213> ORGANISM: Bifidobacterium animalis

<400> SEQUENCE: 13
ctctcgtcaa gcagcttgtc g                                             21

<210> SEQ ID NO 14
<211> LENGTH: 21
<212> TYPE: DNA
<213> ORGANISM: Bifidobacterium animalis

<400> SEQUENCE: 14
ggccgtctgg tcttccgcat t                                             21
```